US009181040B2

(12) United States Patent
Murakami et al.

(10) Patent No.: US 9,181,040 B2
(45) Date of Patent: Nov. 10, 2015

(54) METHOD FOR CHANGING A TRANSPORTING CONFIGURATION OF A WORKPIECE OF AN ABSORBENT ARTICLE

(75) Inventors: Seiji Murakami, Kagawa (JP); Youji Shinomori, Kagawa (JP); Hidenori Sato, Kagawa (JP); Masashi Hosokawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 108 days.

(21) Appl. No.: 13/982,656

(22) PCT Filed: Jan. 24, 2012

(86) PCT No.: PCT/JP2012/051440
§ 371 (c)(1),
(2), (4) Date: Nov. 19, 2013

(87) PCT Pub. No.: WO2012/105374
PCT Pub. Date: Aug. 9, 2012

(65) Prior Publication Data
US 2014/0060999 A1 Mar. 6, 2014

(30) Foreign Application Priority Data
Jan. 31, 2011 (JP) ................................. 2011-018701

(51) Int. Cl.
B65G 47/26 (2006.01)
A61F 13/15 (2006.01)
(Continued)

(52) U.S. Cl.
CPC .......... *B65G 47/26* (2013.01); *A61F 13/15764* (2013.01); *A61F 13/15804* (2013.01); *A61F 13/47* (2013.01); *A61F 13/472* (2013.01); *A61F 2013/4708* (2013.01)

(58) Field of Classification Search
CPC ............ B65G 47/26; A61F 2013/4708; A61F 13/15764
USPC ........................................ 198/418.7, 458, 448
See application file for complete search history.

(56) References Cited

U.S. PATENT DOCUMENTS 2,621,774 A * 12/1952 Rourke .......................... 198/433
2,951,574 A * 9/1960 Craig .......................... 198/836.3
(Continued)

FOREIGN PATENT DOCUMENTS

CN 1612803 A 5/2005
JP 09322909 A 12/1997
(Continued)

OTHER PUBLICATIONS

Office Action issued Jul. 2, 2014, corresponds to Chinese patent application No. 201280007076.6.
(Continued)

*Primary Examiner* — William R Harp
(74) *Attorney, Agent, or Firm* — Hauptman Ham, LLP

(57) ABSTRACT

A method of changing a transporting configuration of a workpiece of an absorbent article includes: for the workpiece having a shape in which a longitudinal central section is narrower in the lateral direction than longitudinal end sections, transporting a plurality of workpieces in longitudinal-direction flowing, the plurality of workpieces being transported in a state where the longitudinal end sections of each workpiece are adjacent to the central section of another workpiece and the plurality of workpieces form N workpiece lines (N is an integer of 2 or more) arranged in a lateral direction; forming each workpiece group including N workpieces by correlating, based on a predetermined correlation pattern; and changing a transporting configuration of the workpieces of the workpiece group from the longitudinal-direction flowing to the lateral-direction flowing. The forming of the workpiece group is performed by correlating workpieces arranged side by side in the lateral direction.

2 Claims, 10 Drawing Sheets

(51) Int. Cl.
*A61F 13/472* (2006.01)
*A61F 13/47* (2006.01)

(56) References Cited

U.S. PATENT DOCUMENTS

| | | | | |
|---|---|---|---|---|
| 3,179,231 | A * | 4/1965 | Craig | 198/433 |
| 3,444,980 | A * | 5/1969 | Wiseman | 198/445 |
| 3,461,766 | A | 8/1969 | Anderson | |
| 4,129,207 | A * | 12/1978 | Cupp | 198/445 |
| 6,202,827 | B1 * | 3/2001 | Drewitz | 198/433 |
| 6,688,456 | B2 * | 2/2004 | Jones et al. | 198/415 |
| 6,913,718 | B2 * | 7/2005 | Ducker et al. | 264/37.1 |
| 8,739,960 | B2 * | 6/2014 | Eschlbeck | 198/429 |
| 2003/0087056 | A1 | 5/2003 | Ducker et al. | |

FOREIGN PATENT DOCUMENTS

| | | |
|---|---|---|
| JP | 2004196389 A | 7/2004 |
| JP | 2005508226 A | 3/2005 |
| WO | 2005079721 A1 | 9/2005 |

OTHER PUBLICATIONS

International Search Report corresponding to PCT/JP2012/051440 dated May 1, 2012.

* cited by examiner

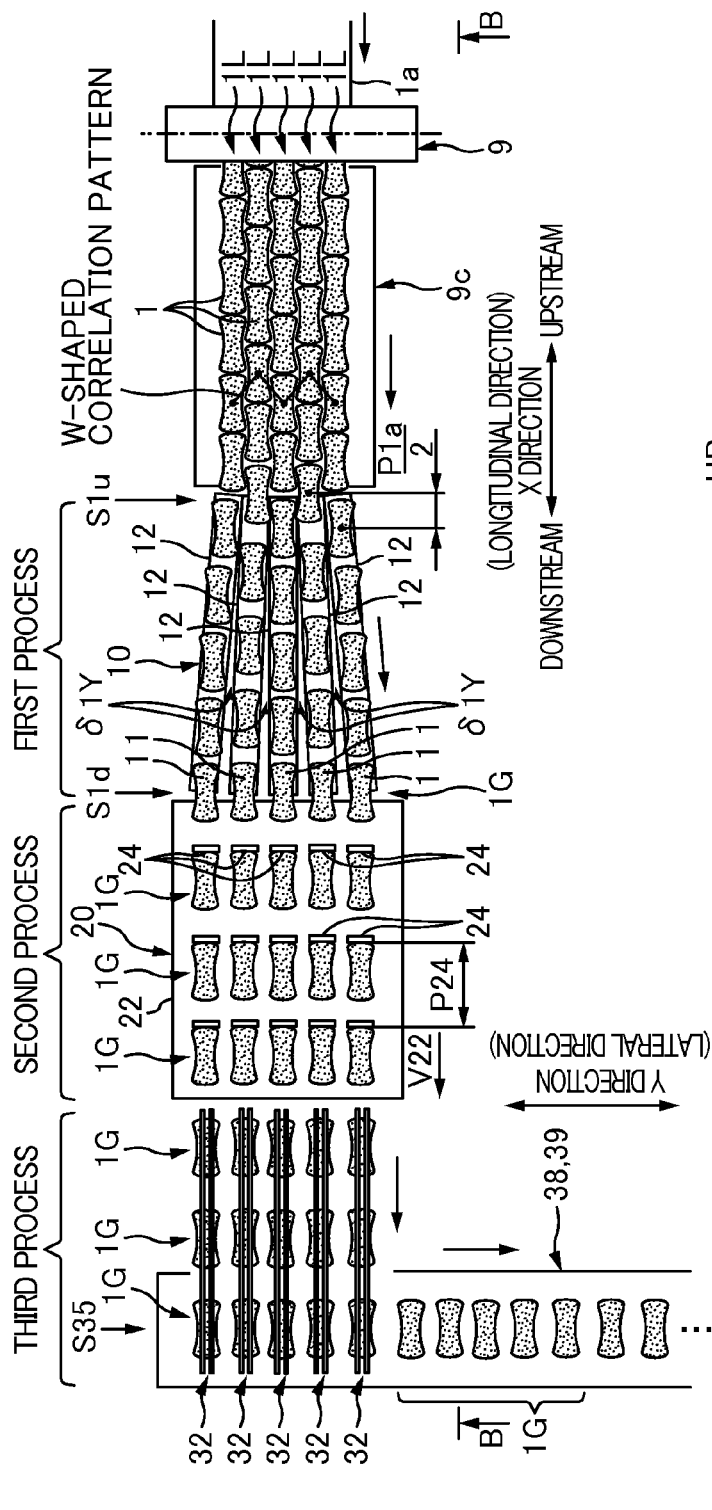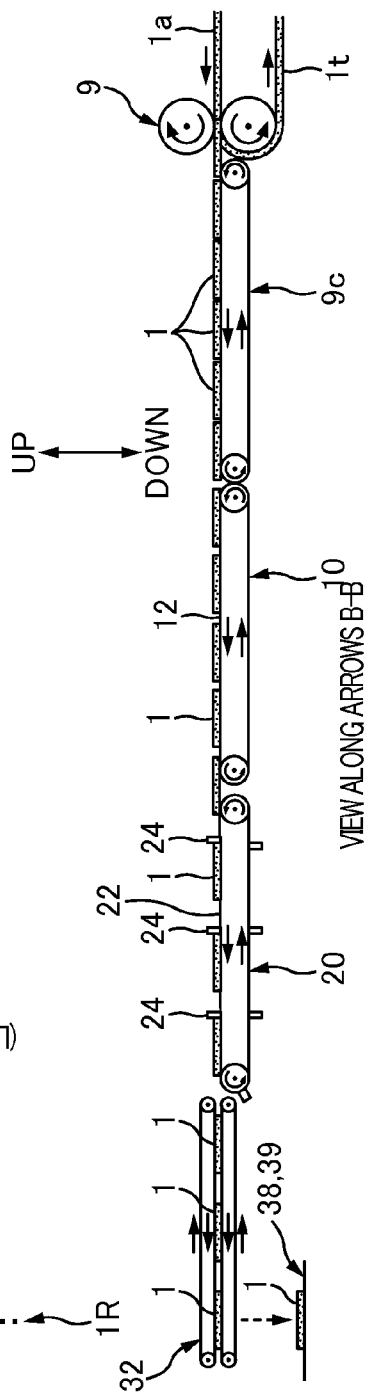
FIG. 3A
FIG. 3B

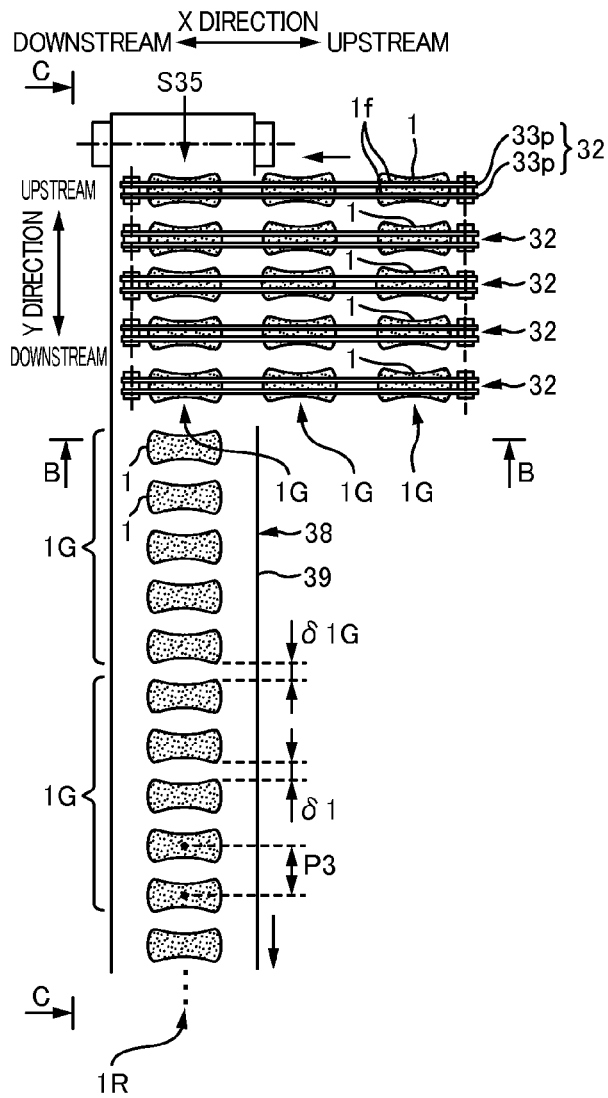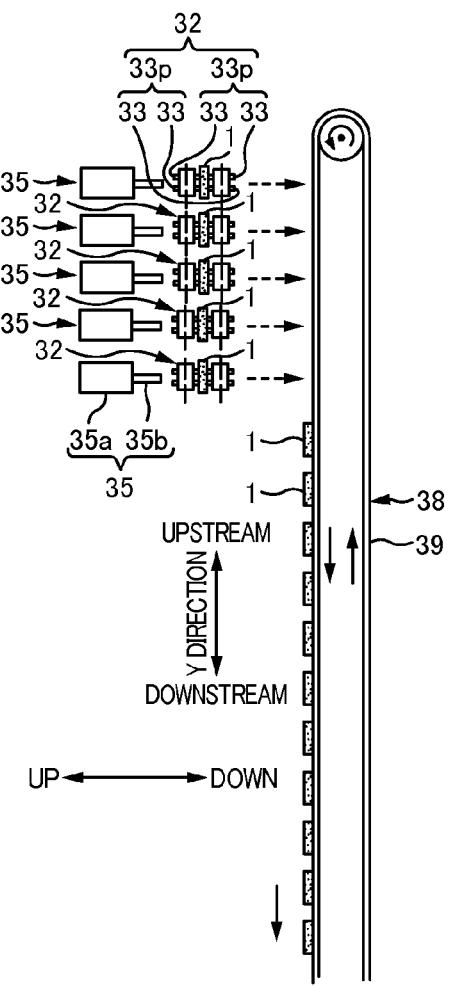
FIG. 4A
FIG. 4C
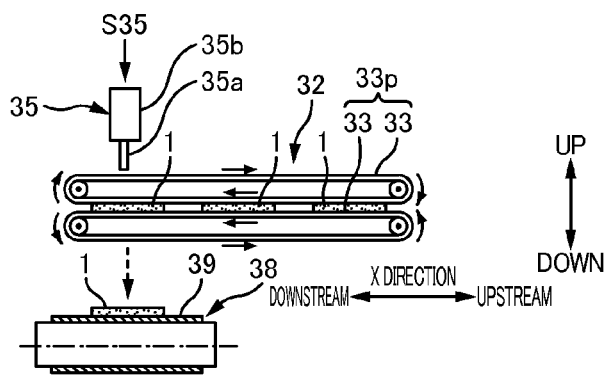
FIG. 4B

METHOD FOR CHANGING A TRANSPORTING CONFIGURATION OF A WORKPIECE OF AN ABSORBENT ARTICLE

RELATED APPLICATIONS

The present application is a National Phase of PCT/JP2012/051440,filed Jan. 24, 2012, and is based on, and claims priority from, Japanese application No. 2011-018701 filed Jan. 31, 2011.

TECHNICAL FIELD

The invention relates to a method for changing a transporting configuration of a workpiece of an absorbent article such as a sanitary napkin from longitudinal-direction flowing to lateral-direction flowing.

BACKGROUND ART

As examples of an absorbent article that absorbs liquid such as menstrual blood, known are sanitary napkins, panty liners, and the like. The planar shape of the main body (hereinafter referred to as a workpiece) of such absorbent articles is generally one in which the longitudinal central section 1c of the workpiece 1 is narrower in the lateral direction than the longitudinal end sections 1e and 1e of the workpiece 1 (i.e., FIG. 1A).

As a method for manufacturing such workpieces 1, 1 . . . , [PTL 1] describes that workpieces 1, 1 . . . are produced by die-cutting a continuous sheet by using a die-cutter roll device while the continuous sheet are being transported in a transporting direction, which is the longitudinal direction of the workpiece 1. Also, [PTL 1] describes that these workpieces 1, 1 . . . are die-cut in a certain die-cutting pattern which is for reducing die-cut chips (chips).

The die-cutting pattern is a so-called zig zag arrangement pattern (i.e., FIG. 2A). That is, in the pattern, a plurality of workpiece lines 1L, 1L . . . (5 lines in FIG. 2A) are arranged in the lateral direction, each of the workpiece lines 1L including a plurality of workpieces 1, 1 . . . arranged along the longitudinal direction. In addition, in the pattern, the longitudinal end sections 1e and 1e of each workpiece 1 are adjacent to the longitudinal central section 1c of another workpiece 1 that is adjacent to the workpiece 1 in the lateral direction.

After the die-cutting, the workpieces 1, 1 . . . are transported along the longitudinal direction of the workpieces 1 while remaining being arranged in the foregoing die-cutting pattern. That is, the workpieces 1, 1 . . . are transported in longitudinal-direction flowing, in which the napkins 1 is transported along the longitudinal direction thereof.

On the other hand, though, at the time of individual wrapping of such a workpiece 1, workpiece 1 is tri-folded usually by being folded at two longitudinal positions, [PTL 2] discloses a method for tri-folding as follows: workpieces 1, 1 . . . are transported in lateral-direction flowing (transported along the lateral direction of the workpieces 1, 1 . . . ), and the longitudinal end sections 1e and 1e of each workpiece 1 are tri-folded together with a wrapping sheet 7 by passing sequentially the workpieces 1, 1 . . . through the position of a folding-guide member (i.e., FIG. 2B).

CITATION LIST

Patent Literature

[PTL 1] Japanese Unexamined Patent Application Publication (Translation of PCT Application) No. 2005-508226.

[PTL 2] Japanese Patent Application Laid-open Publication No. 9-322909

SUMMARY OF THE INVENTION

Technical Problem

However, neither of [PTL 1] and [PTL 2] disclose a method in which the transporting configuration of workpieces 1 changes to lateral-direction flowing from longitudinal-direction flowing in which the workpieces 1 are transported in a form of a plurality of workpiece lines 1L, 1L . . . as mentioned above. A method has been desired in which the transporting configuration can be changed smoothly.

The invention has been made in view of the above conventional problems, and an advantage thereof is to provide a method in which the transporting configuration of workpieces changes smoothly to lateral-direction flowing from longitudinal-direction flowing in which the workpieces are transported in a form of a plurality of workpiece lines.

Solution to Problem

An aspect of the invention to achieve the above advantage is a method for changing a transporting configuration of a workpiece of an absorbent article, in which the transporting configuration is changed from longitudinal-direction flowing to lateral-direction flowing, the workpiece having a shape in which a longitudinal central section is narrower in the lateral direction than longitudinal end sections, the workpiece being transported in the longitudinal-direction flowing along a longitudinal direction of the workpiece, the workpiece being transported in the lateral-direction flowing along a lateral direction of the workpiece, the method including:

transporting a plurality of workpieces in longitudinal-direction flowing, the plurality of workpieces being transported in a state where the longitudinal end sections of each workpiece are adjacent to the central section of another workpiece that is adjacent in the lateral direction and the plurality of workpieces form N workpiece lines (N is an integer of 2 or more) arranged in the lateral direction, each of the workpiece lines including a plurality of the workpieces along the longitudinal direction;

forming each workpiece group including N workpieces by correlating, based on a predetermined correlation pattern, the N workpieces respectively belonging to different workpiece lines of the N workpiece lines that are transported in the longitudinal-direction flowing, the forming of the workpiece group being performed by correlating, based on the correlation pattern, workpieces that are arranged side by side in the lateral direction; and changing a transporting configuration of the workpieces of the workpiece group from the longitudinal-direction flowing to the lateral-direction flowing, the changing being performed for the each workpiece group.

Other features of this invention will become apparent from the description in this specification and the attached drawings.

Effects of the Invention

According to the invention, it is possible to provide a method in which the transporting configuration of work-

BRIEF DESCRIPTION OF THE DRAWINGS

FIG. 3A is a schematic plan view showing the arrangement of apparatuses associated with a transporting-configuration change process according to the first embodiment, and FIG. 3B is a schematic side view thereof, which is a view along arrows B-B in FIG. 3A.

FIG. 4A is a schematic plan view showing the arrangement of apparatuses of the third process, FIG. 4B is a view along arrows B-B in FIG. 4A, and FIG. 4C is a view along arrows C-C in FIG. 4A.

FIG. 8C is a schematic elevation of the outer circumferential surface of the rotating drum 111 after enlarging the arrangement pitch P1a.

MODE FOR CARRYING OUT THE INVENTION

Figure 1:
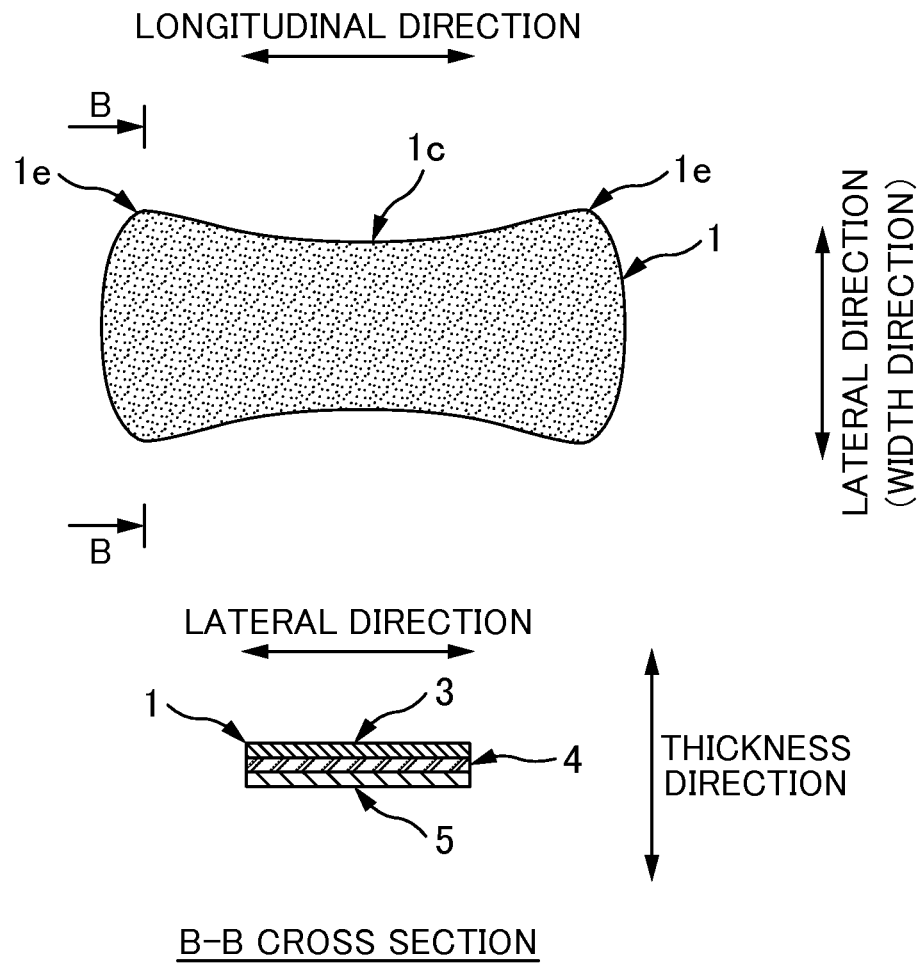
FIG. 1A is a plan view of a thin napkin 1, which is an example of a workpiece 1.
FIG. 1B is a view along arrows B-B in FIG. 1A.

At least the following matters will be made clear by the description in the present specification and the accompanying drawings.

A method for changing a transporting configuration of a workpiece of an absorbent article, in which the transporting configuration is changed from longitudinal-direction flowing to lateral-direction flowing, the workpiece having a shape in which a longitudinal central section is narrower in the lateral direction than longitudinal end sections, the workpiece being transported in the longitudinal-direction flowing along a longitudinal direction of the workpiece, the workpiece being transported in the lateral-direction flowing along a lateral direction of the workpiece, the method including:

transporting a plurality of workpieces in longitudinal-direction flowing, the plurality of workpieces being transported in a state where the longitudinal end sections of each workpiece are adjacent to the central section of another workpiece that is adjacent in the lateral direction and the plurality of workpieces form N workpiece lines (N is an integer of 2 or more) arranged in the lateral direction, each of the workpiece lines including a plurality of the workpieces along the longitudinal direction;

forming each workpiece group including N workpieces by correlating, based on a predetermined correlation pattern, the N workpieces respectively belonging to different workpiece lines of the N workpiece lines that are transported in the longitudinal-direction flowing, the forming of the workpiece group being performed by correlating, based on the correlation pattern, workpieces that are arranged side by side in the lateral direction; and changing a transporting configuration of the workpieces of the workpiece group from the longitudinal-direction flowing to the lateral-direction flowing, the changing being performed for the each workpiece group.

With such a method for changing a transporting configuration of a workpiece of an absorbent article, the transporting configuration is changed, for each workpiece group, from longitudinal-direction flowing to lateral-direction flowing. That is, by applying the same change operation to the workpiece groups, the transporting configuration of all workpieces can be changed. This makes it possible to smoothly change the transporting configuration.

Further, the forming of the workpiece group is performed by correlating the workpieces that are arranged side by side. Therefore, since the correlated workpieces are closely located, it is easy to arrange the workpieces belonging to the workpiece group along the transporting direction in the lateral-direction flowing. This makes it possible to smoothly change the transporting configuration to the lateral-direction flowing.

In such a method for changing a transporting configuration of a workpiece, it is desirable that in the changing of the transporting configuration for each workpiece group from the longitudinal-direction flowing to the lateral-direction flowing, a space in the lateral direction between the workpieces belonging to the workpiece group is enlarged, and after aligning positions of all of the workpieces belonging to the workpiece group in a transporting direction of the workpieces, the transporting direction of the workpieces is changed to a direction perpendicular to a direction in which the workpieces is transported in the longitudinal-direction flowing, at the same time for all of the workpieces.

With such a method for changing a transporting configuration of a workpiece of an absorbent article, a space in the lateral direction between the workpieces belonging to the workpiece group is enlarged. In addition, after aligning positions of all of the workpieces belonging to the workpiece group in the transporting direction of the workpieces, the transporting direction of the workpieces is changed to a direction perpendicular to the direction in which the workpieces is transported in the longitudinal-direction flowing, at the same time for all of the workpieces. This reliably makes it possible to change transportation of the workpiece group from longitudinal-direction flowing to lateral-direction flowing. Thus, if this operation is repeatedly performed for each workpiece group, the transporting configuration of all workpieces is smoothly changed from longitudinal-direction flowing to lateral-direction flowing.

In such a method for changing a transporting configuration of a workpiece, it is desirable that in the changing of the transporting configuration for each workpiece group from the longitudinal-direction flowing to the lateral-direction flowing, a longitudinal direction of the workpieces belonging to the workpiece group that are being transported in the longitudinal-direction flowing is changed to a direction perpendicular to the longitudinal direction, and the workpieces are aligned so that the workpieces are in a same position in the longitudinal direction.

With such a method for changing a transporting configuration of a workpiece of an absorbent article, the longitudinal direction of the workpieces belonging to the workpiece group that are being transported in the longitudinal-direction flowing is changed to the direction perpendicular to the longitudinal direction. In addition, the workpieces are aligned so that the workpieces are in the same position in the longitudinal direction. This reliably makes it possible to change transportation of the workpiece group from longitudinal-direction flowing to lateral-direction flowing. Thus, if this operation is repeatedly performed for each workpiece group, the transporting configuration of all workpieces is smoothly changed from longitudinal-direction flowing to lateral-direction flowing.

In such a method for changing a transporting configuration of a workpiece, it is desirable that in the forming of the workpiece group based on the correlation pattern, as for odd workpiece lines of the N workpiece lines, certain workpieces whose positions in a direction in which the certain workpieces are transported in the longitudinal-direction flowing are the same are correlated as workpieces belonging to a same workpiece group, and as for even workpiece line, a workpiece adjacent to any of the certain workpieces is correlated as a workpiece belonging to the same workpiece group.

With such a method for changing a transporting configuration of a workpiece of an absorbent article, it is more reliably possible to change transportation of the workpieces of the workpiece group from longitudinal-direction flowing to lateral-direction flowing by means such as changing the transporting direction of the workpieces to the direction perpendicular to the direction in which the workpieces is transported in the longitudinal-direction flowing, at the same time for all of the workpieces.

In such a method for changing a transporting configuration of a workpiece, it is desirable that in the forming of the workpiece group based on the correlation pattern, from a workpiece line on one end to a workpiece line on the other end in a lateral direction of the workpieces that are being transported in the longitudinal-direction flowing, workpieces which are sequentially adjacent to obliquely upstream are correlated as workpieces belonging to a same workpiece group.

With such a method for changing a transporting configuration of a workpiece of an absorbent article, it is more reliably possible to change transportation of the workpieces of the workpiece group from longitudinal-direction flowing to lateral-direction flowing by means such as changing the longitudinal direction of the workpieces that are being transported in the longitudinal-direction flowing to the direction perpendicular to the longitudinal direction in which the workpieces is transported in the longitudinal-direction flowing.

First Embodiment 2

A method for changing the transporting configuration of workpieces 1 according to the first embodiment is used for manufacturing a thin napkin 1, which is an example of an absorbent article.

FIG. 1A is a plan view of a thin napkin 1, and FIG. 1B is a view along arrows B-B in FIG. 1A.

A thin napkin 1 is a sheet-like member which is substantially in hourglass shape when viewed from above, and has the longitudinal direction and the lateral direction (width direction) which are perpendicular to each other. The napkin 1 has a three-layer structure in the thickness direction; that is, a liquid-absorbing sheet 4 which absorbs liquid is placed between a liquid-permeable surface sheet 3 and a liquid-impermeable back face sheet 5, and portions of these sheets which face each other are joined and integrated.

As an example of the surface sheet 3, provided is nonwoven fabric made of plastic fiber, etc. As an example of the back face sheet 5, provided is synthetic resin film, etc. And, as an example of the liquid-absorbing sheet 4, provided is air-laid nonwoven fabric made of cellulose fiber, etc. However, this invention is not limited thereto.

Because the napkin 1 is attached to the crotch section of an undergarment for use, the outer shape of the napkin 1 is substantially in hourglass shape as mentioned above. In other words, a longitudinal central section $1c$ is narrower in the lateral direction than longitudinal end sections $1e$ and $1e$.

Figure 2A:
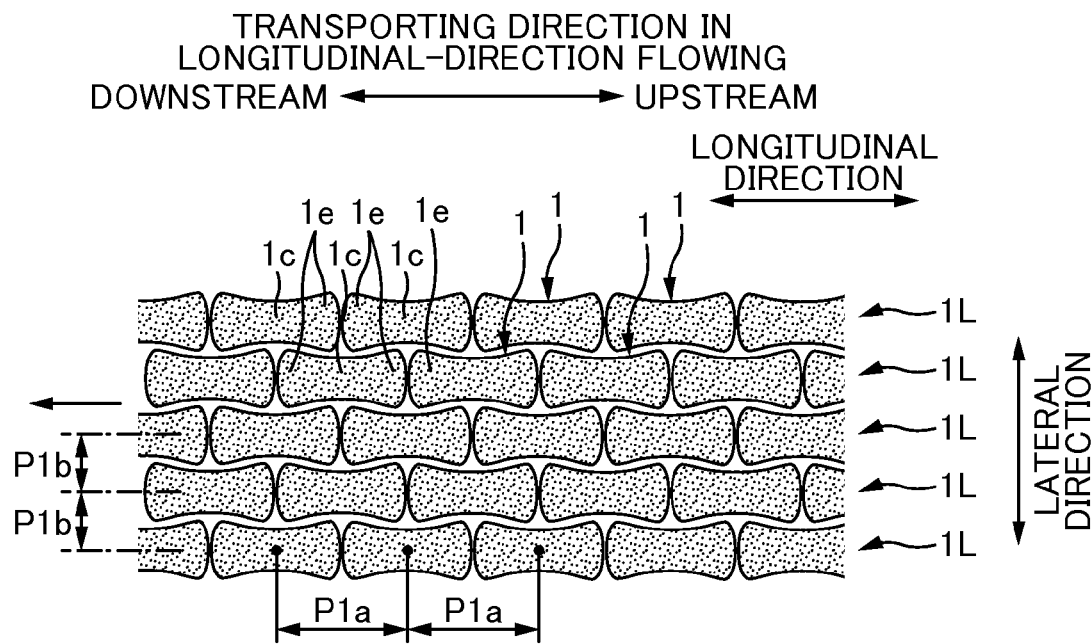
FIG. 2A is a schematic plan view of napkins 1, 1 . . . that have just been die-cut and are transported in longitudinal-direction flowing while being positioned in zig zag arrangement.

Such a napkin 1 (corresponding to a workpiece) is manufactured by die-cutting a continuous sheet $1a$ (FIG. 3A) by using a die-cutter roll device 9 (FIG. 3A) while a continuous sheet $1a$ being transported in the continuing direction of the sheet $1a$; the continuous sheet $1a$ has a three-layer structure in which the surface sheet 3, the liquid-absorbing sheet 4 and the back face sheet 5 mentioned above are stacked. In order to reduce die-cut chips it (FIG. 3B), the continuous sheet $1a$ is die-cut in a certain die-cutting pattern. The die-cutting pattern is a so-called zig zag arrangement pattern. That is, as shown in FIG. 2A, in the pattern, N napkin lines 1L (corresponding to a workpiece line) are arranged in the lateral direction at a certain pitch P1$b$ (N is an integer of 2 or more; 5 in this example), each of the napkin lines 1L including a plurality of napkins 1, 1 . . . arranged along the longitudinal direction at a certain arrangement pitch P1$a$. Concerning napkin lines 1L and 1L adjacent in the lateral direction, the positions in the longitudinal direction of the napkins 1 are shifted in relation to each other by half the arrangement pitch P1$a$ (=P1$a$/2). Thus, in the pattern, the longitudinal end sections 1$e$ and 1$e$ of each napkin 1 are adjacent to the longitudinal central section 1$c$ of another napkin 1 that is adjacent to the napkin 1 in the lateral direction.

After the die-cutting, napkins 1, 1 . . . are separated from die-cut chips it (FIG. 3B), and these napkins 1, 1 . . . are transported along their longitudinal direction while being arranged in a zig zag arrangement, which is the foregoing die-cutting pattern, as shown in FIG. 2A. That is, the napkins 1, 1 . . . are transported in longitudinal-direction flowing, in which the napkins 1 is transported along the longitudinal direction thereof.

Figure 2B:
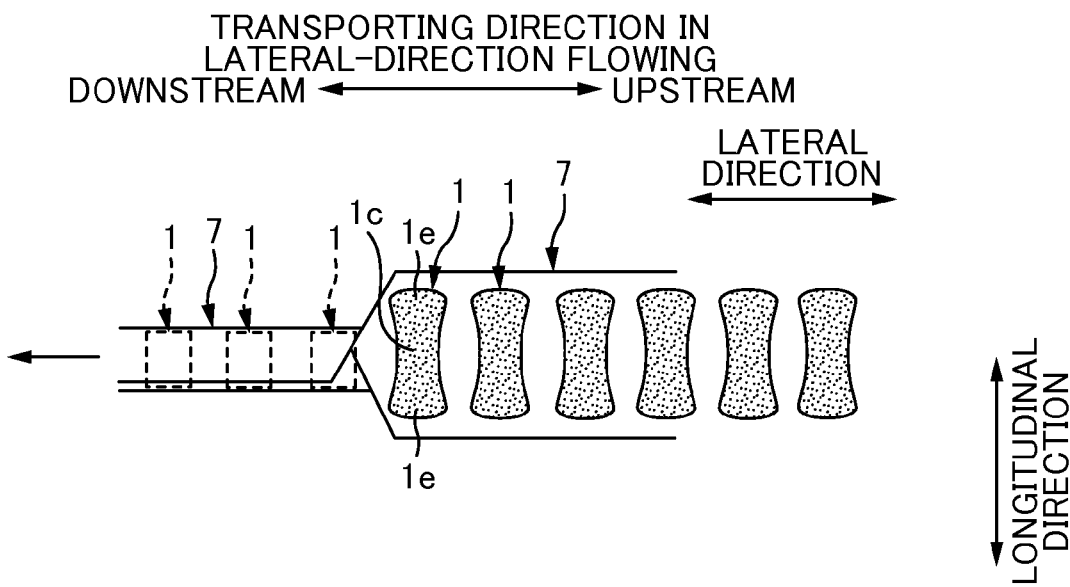
FIG. 2B is a schematic plan view of napkins 1, 1 . . . that are transported in lateral-direction flowing in order to be subject to individual wrapping.

However, as mentioned above, the individual wrapping of napkins 1, which is performed after the foregoing process, is performed under a condition that the napkins 1 are transported in lateral-direction flowing. More specifically, as shown in FIG. 2B, napkins 1, 1 . . . are arranged in a straight line (in a single line) along the lateral direction and they are transported along the lateral direction. In other words, the napkins 1 are transported in lateral-direction flowing. While being transported in lateral-direction flowing, napkins 1 meet a wrapping sheet 7 which is in the form of a continuous sheet and comes from below, for example; and thereafter, the napkins 1 pass a folding-guide member (not shown) provided at a predetermined position in the transporting direction of lateral-direction flowing. At this time, the longitudinal end sections 1e and 1e of each napkin 1 are respectively folded together with the wrapping sheet 7, which results in the tri-folded napkin 1.

Thus, between a die-cutting process and an individual-wrapping process, provided is a transporting-configuration change process in which the transporting configuration of napkins 1 is changed from longitudinal-direction flowing to lateral-direction flowing.

FIGS. 3A and 3B are explanatory diagrams of this transporting-configuration change process. FIG. 3A is a schematic plan view showing the arrangement of apparatuses associated with the process, and FIG. 3B s a schematic side view thereof, which is a view along arrows B-B in FIG. 3A.

In this example, a belt conveyor 9c transports napkins 1, 1 . . . in longitudinal-direction flowing in the foregoing zig zag arrangement; the napkins 1, 1 . . . are transported from the die-cutter roll device 9 in the preceding process to the transporting-configuration change process. Then, in the transporting-configuration change process, the transporting configuration of these napkins 1 is changed to lateral-direction flowing, in which the napkins 1 are arranged in a line and whose transporting direction is perpendicular to in the transporting direction in longitudinal-direction flowing. The napkins 1 are sent to the subsequent individual-wrapping process.

In the following description, the transporting direction in longitudinal-direction flowing is referred to as an X direction, and the transporting direction in lateral-direction flowing is referred to as a Y direction. The X direction is parallel to the longitudinal direction of a napkin 1 at both time of longitudinal-direction flowing and lateral-direction flowing. The Y direction is parallel to the lateral direction of a napkin 1 at both time of longitudinal-direction flowing and lateral-direction flowing. That is, during the transporting-configuration change process, the transporting configuration of napkins 1 is changed from longitudinal-direction flowing to lateral-direction flowing, which is realized by changing only the transporting direction from the X direction to the Y direction while maintaining the longitudinal direction of each napkin 1 in the X direction.

The foregoing transporting-configuration change process has a first process to a third process.

In the first process, napkins 1, 1 . . . that are arranged in zig zag arrangement and transported in longitudinal-direction flowing are received and transported in the X direction, which is the transporting direction of longitudinal-direction flowing. Simultaneously, enlarged is a space δ1Y in the lateral direction between adjacent napkin lines 1L and 1L; the lateral direction is the Y direction. Substantially simultaneously with this, the positions in the X direction for the napkins 1 of all napkin lines 1L, 1L . . . are adjusted until the napkins have reached a downstream-end position S1d of the first process. Thereby, at the downstream-end position S1d of the first process, positions in the X direction for napkins 1 of all napkin lines 1L, 1L . . . (i.e., positions of the downstream ends of the napkins 1) are substantially aligned.

Such a first process is realized by, for example, a widening conveyor 10. The widening conveyor 10 has endless conveyor belts 12 each of which is set for each of napkin lines 1L. Each conveyor belt 12 is driven and moved circumferentially to form the transport path of the napkins 1 on its upper surface, for example. The conveyor belt 12 located at the center in the Y direction serves as a transport path parallel to the X direction. The conveyor belts 12, 12 . . . on both side thereof serve as transport paths inclined at a predetermined angle θ of inclination with respect to the X direction so that they orient outwardly with respect to the Y direction (towards the end sides) as they go downstream in the X direction. Further, the angle θ gradually becomes larger as the conveyor belt 12 is located outwards in the Y direction (on the end sides). Thus, as napkins 1 are transported more downstream in the X direction by these conveyor belts 12, 12 . . . , the spaces δ1Y between napkin lines 1L and 1L gradually become larger.

Further, the conveyor belts 12 for even napkin lines 1L are rotating faster than conveyor belts 12 for odd napkin lines 1L. This enables the widening conveyor 10 to perform as follows: the widening conveyor 10 receives napkins 1, 1 . . . at an upstream-end position S1u; at this stage, napkins 1 of even lines are being transported with delay (positioned upstream in the X direction) corresponding to half the arrangement pitch P1a (=P1a/2); the napkins 1 of the even lines substantially catch up with the napkins 1 of odd lines at the time when the napkins 1 of the even lines have reached the downstream-end position S1d. As a result, the positions in the X direction for the napkins 1 of all napkin lines 1L, 1L . . . are substantially aligned at the downstream-end position S1d, whether the napkin is in odd line or even line.

In this example, napkins 1 of even lines catch up with napkins 1 of odd lines. However, the reversed relation may be employed. In such a case, the conveyor belts 12 for the odd lines rotate faster than the conveyor belts 12 for the even lines.

Further, as mentioned above, the spaces δ1Y in the lateral direction, which is the Y direction, become larger based on the angle θ. This makes it possible to effectively avoid interference that is caused on the end sections 1e and 1e of napkins 1 and 1 when napkins 1 of the even lines catch up with napkins 1 of the odd lines.

In the subsequent processes, a row of napkins 1, 1 . . . along the lateral direction whose positions in the X direction are aligned are treated as a group of napkins 1 belonging to the same napkin group 1G. Note that this napkin group 1G corresponds to a "workpiece group".

Incidentally, as is apparent from the above description, it can be said that such a napkin group 1G is formed by grouping five napkins 1, 1 . . . each of which belongs to a different napkin line 1L of five napkin lines 1L, 1L . . . . At the time point immediately before this first process, napkins 1, 1 . . . belonging to the same napkin group 1G are in the following positional relationships. That is, as for napkins 1, 1 . . . belonging to odd napkin lines 1L, 1L . . . , their positions in the X direction (the transporting direction in longitudinal-direction flowing) are the same. On the other hand, as for napkins 1, 1 . . . belonging to even napkin lines 1L and 1L, the napkins 1, 1 . . . are adjacent in the Y direction to the napkins 1 belonging to odd napkin lines 1L, 1L . . . ; the positions in the X direction for napkins 1, 1 ... belonging to even napkin lines are shifted upstream by half the arrangement pitch P1a (=P1a/2).

Therefore, it can be said that in longitudinal-direction flowing at the time point immediately before the first process, the napkins 1, 1 ... belonging to the same napkin group 1G are grouped based on a W-shaped correlation pattern. More generally, it can be said that napkins 1 and 1 which are adjacent to each other in the Y direction (the lateral direction) are correlated based on foregoing correlation pattern. That is, it can be said that the foregoing first process is performed for each napkin group 1G.

In this example, the number of napkin lines 1L, 1L ... in longitudinal-direction flowing is five. However, the invention is not limited to five lines. Any number of lines other than five lines may be employed as long as the number of lines is two or more.

In the second process, the napkins 1, 1 ... of each napkin group 1G are received together from the downstream-end position S1d in the first process. In addition, the positions in the X direction of the napkins 1, 1 of the received napkin group 1G ... are adjusted more precisely.

Such a second process is realized by an attach conveyor 20. In order to make it possible to simultaneously transport the napkins 1, 1 ... belonging to the same napkin group 1G, the attach conveyor 20 has a single, endless conveyor belt 22 that is wide in the Y direction. The conveyor belt 22 is driven and moves circumferentially so that its upper surface serves as a transport path. On the belt surface of the conveyor belt 22, a plurality of claws 24, 24 ... arranged in a straight line along the Y direction are projected at a predetermined pitch P24 in the X direction; the pitch P24 corresponds to the transport pitch of the napkin groups 1G in the X direction. Further, the circumferential speed V22 of the conveyor belt 22 is set to be slightly faster than the circumferential speed of the conveyor belts 12 for even napkin lines 1L of the foregoing widening conveyor 10 (that is, faster conveyor belts 12 of the widening conveyor 10; the conveyor belts 12 for the odd lines in the case where napkins 1 of odd lines catch up with napkins 1 of even lines as described in the foregoing reversed relation, because the conveyor belts 12 for the odd lines are running faster). Thus, the napkins 1, 1 ... of the napkin group 1G which transfers from the widening conveyor 10 to the attach conveyor 20 are transported while being pushed from behind by the claws 24 of the conveyor belt 22; thereby, the positions in the X direction of the napkins 1, 1 ... are corrected by the claws 24. As a result, the positions in the X direction of all napkins 1, 1 ... belonging to the napkin group 1G are adjusted precisely.

In the third process, the transporting directions of the napkins 1, 1 ... of each napkin group 1G that is received from the second process change at the same time from the X direction to the Y direction. Thereby, the napkins 1, 1 ... of each napkin group 1G are transported in the Y direction while maintaining the napkins 1, 1 ... arranged in a line along the Y direction. At this stage, the longitudinal directions of the napkins 1, 1 ... remain in the X direction. Therefore, the napkin group 1G is now transported in lateral-direction flowing.

FIGS. 4A to 4C are enlarged views of the third process. FIG. 4A is a schematic plan view showing the arrangement of apparatuses of the third process, FIG. 4B is a view along arrows B-B in FIG. 4A, and FIG. 4C is a view along arrows C-C in FIG. 4A.

Such a third process is realized by combining the X-direction conveying mechanisms 32, 32 ... and the Y-direction conveying mechanism 38: the X-direction conveying mechanisms 32, 32 ... which transport napkins 1 in the X direction while supporting the napkins 1 so that the napkins 1 can drop; and the Y-direction conveying mechanism 38 that includes a horizontal transport path along the Y direction and that is disposed below the X-direction conveying mechanism 32, 32 ... having a grade separation at points of intersection with the X-direction conveying mechanism 32, 32 ....

As shown in FIG. 4A, the X-direction conveying mechanisms 32 are provided for each napkin 1 of a napkin group 1G. Each of the X-direction conveying mechanisms 32 has a pair of upper and lower transporting cords 33 and 33, and supports a napkin 1 by sandwiching it with the pair of upper and lower transporting cords 33 and 33, as shown in FIG. 4B. Also, as shown in FIGS. 4A and 4C, a transporting cord pair 33P, which is composed of the pair of upper and lower transporting cord 33 and 33, is provided on each of end sections if and if in the Y direction, which is the lateral direction of the napkins 1. Thereby, while each napkin 1 are supported by the end sections if and if in the lateral direction of the napkin 1, the napkin 1 is transported downstream in the X direction by motion of transporting cords 33 and 33 that are driven.

At a predetermined position S35 which is located downstream in the X direction, defined is a dropping position S35 at which napkins 1, 1 ... of the napkin group 1G that has reached the position S35 are dropped downwardly at the same time. Thereby, all napkins 1, 1 ... belonging to the same napkin group 1G drop substantially simultaneously from the transporting cord pair 33P, and land on the transport path of the Y-direction conveying mechanism 38 located below. Thereby, the transporting direction of the napkin group 1G changes at the same time from the X direction to the Y direction. At this stage, the lateral direction of the napkins 1, 1 ... of the napkin group 1G is maintained in the Y direction without change. Therefore, the foregoing change of the transporting direction results in change of the transporting configuration of a napkin group 1G from longitudinal-direction flowing to lateral-direction flowing. Thereafter, while keeping in lateral-direction flowing, the napkins 1, 1 ... of each napkin group 1G are transported to the subsequent individual-wrapping process, and are subjected to such a process as the abovementioned tri-folding.

The dropping is performed by a dropping mechanism 35 shown in FIGS. 4B and 4C. The dropping mechanism 35 is provided for each napkin 1 above the foregoing dropping position S35. Each dropping mechanism 35 has a pusher bar 35a that emerges downwardly. Every time when a napkin group 1G reaches the foregoing dropping position S35, the pusher bar 35a repeatedly emerges due to a suitable power source 35b such as an air cylinder. Note that, instead of such a dropping mechanism 35, ejecting of air may be used to fall a napkin 1 downwardly. In this case, air-nozzles that eject air downwards are provided above the dropping position S35, and the air-nozzles intermittently eject air towards napkins 1, 1 ... every time when a napkin group 1G reaches the position.

On the other hand, the Y-direction conveying mechanism 38 is a suitable belt conveyor. That is, the Y-direction conveying mechanism 38 includes an endless conveyor belt 39 that are driven and moved circumferentially. On the upper surface of the conveyor belt 39, a transport path is formed along the Y direction by circumferential motion. Thus, napkins 1, 1 ... of the napkin group 1G that drops from dropping position S35 land on the conveyor belt 39 while maintaining the napkins 1, 1 ... in a line along the Y direction. Thereafter, the napkins 1, 1 ... are transported in the Y direction.

The transporting by the Y-direction conveying mechanism 38 is performed in conjunction with the dropping. The detailed description is as follows: the dropping is performed every time when a napkin group 1G has reached the dropping position S35; when the next napkin group 1G has reached the dropping position S35 and is dropped, another napkin group 1G which was dropped immediately before to the transport path of the Y-direction conveying mechanism 38 is promptly transported downstream in the Y direction from the position at where the other napkin group 1G was dropped; and thereby, in the transport path of the Y-direction conveying mechanism 38, an interval δ1G in the Y direction between napkin groups 1G and 1G is maintained in the same size as the interval δ1 between adjacent napkins 1, 1 . . . of each napkin group 1G (see FIGS. 4A and 4C). As a result, the napkins 1, 1 . . . on that transport path are transported with being arranged in a line along the Y direction at a predetermined arrangement pitch P3. Such an adjustment of the interval δ1G in the Y direction between napkin groups 1G and 1G is achieved by adjusting the transport speed of the Y-direction conveying mechanism 38 in the Y direction.

Incidentally, in the foregoing example, as shown in FIGS. 3A and 4A, only one dropping position S35 is set in the X direction, which results in only one napkin line 1R being transported in lateral-direction flowing. However, this invention is not limited thereto. For example, M dropping position s S35 (M is an integer of 2 or more) may be set in the X direction. This makes it possible to transport M napkin lines 1R, 1R . . . in lateral-direction flowing. That is, it is possible to promptly treat a case where there are M lines in the individual-wrapping process. If the number of dropping positions S35, S35 . . . is M, the dropping is performed once every M groups at each dropping position S35 for the napkin group 1G which passes the dropping position S35.

Second Embodiment

Figure 5:
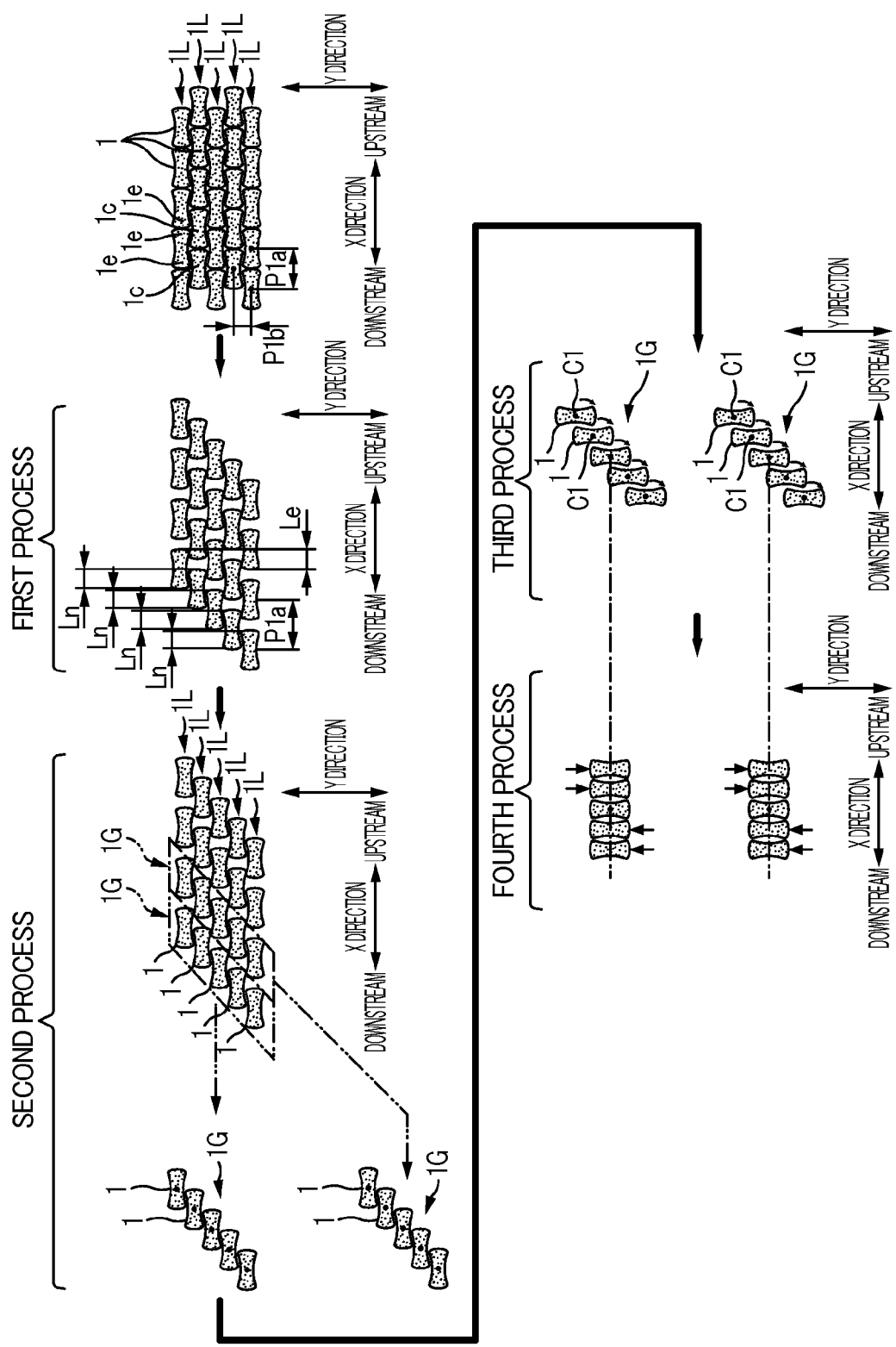
FIG. 5 is an explanatory diagram of a transporting-configuration change process according to the second embodiment.

FIG. 5 is an explanatory diagram of a transporting-configuration change process according to the second embodiment.

In the first embodiment mentioned above, the transporting configuration of napkins 1 is changed from longitudinal-direction flowing to lateral-direction flowing by means such as changing transporting direction from the X direction to the Y direction at the same time for all the napkins of each napkin group 1G while maintaining the longitudinal direction of each napkin 1, which is an example of a workpiece 1. However, in the second embodiment, the transporting configuration of napkins 1 is changed from longitudinal-direction flowing to lateral-direction flowing by means such as changing the longitudinal direction of each napkin 1 from the X direction to the Y direction while maintaining the transporting direction of each napkin 1 without changing it from the X direction to the Y direction. The second embodiment is different from the first embodiment mainly in the foregoing point.

In the following description, a direction which is parallel to the lateral direction of a napkin 1 in longitudinal-direction flowing is also referred to as the Y direction, and any direction perpendicular to the Y direction is also referred to as the X direction. The X direction is also the transporting direction in both of longitudinal-direction flowing and lateral-direction flowing.

The foregoing transporting-configuration change process has a first process to a fourth process.

In the first process, at the first stage, napkins 1, 1 . . . that are arranged in zig zag arrangement and transported in the X direction in longitudinal-direction flowing, as shown in FIG. 5, are received from the die-cutter roll device 109 (FIG. 7) of the preceding process. That is, in the same manner as the abovementioned first embodiment, in the pattern at this stage, N napkin lines 1L, 1L . . . (N is an integer of 2 or more; 5 in this example) are arranged along the Y direction at a certain pitch P1b, each of the napkin lines 1L including a plurality of napkins 1, 1 . . . arranged along the X direction at the arrangement pitch P1a. And, in the pattern, both end sections 1e and 1e of a napkin 1 in the X direction, which is the longitudinal direction thereof, are adjacent to the longitudinal central section 1c of another napkin 1 that is adjacent to the napkin 1 in the Y direction, which is the lateral direction. Thus, these napkins 1, 1 . . . are transported in the X direction. In the first process, napkins 1, 1 . . . that are in this arrangement pattern are received.

While these napkins 1, 1 . . . that is maintained in this arrangement pattern, that is a zig zag arrangement, are being transported in the X direction, the arrangement pitch P1a of each napkin line 1L in the X direction is enlarged. The amount of this enlargement is equal for all napkin lines 1L, 1L . . . , and is determined as follows. That is, the enlargement amount corresponds to one by which an overlapping amount Le in the X direction of the napkins 1 and 1 belonging to the napkin lines 1L and 1L on both ends in the Y direction is equal to an overlapping amount Ln in the X direction of the napkins 1 and 1 adjacent in the Y direction. In other words, the arrangement pitch P1a is enlarged so that the foregoing positional relationship is established.

Figure 6:
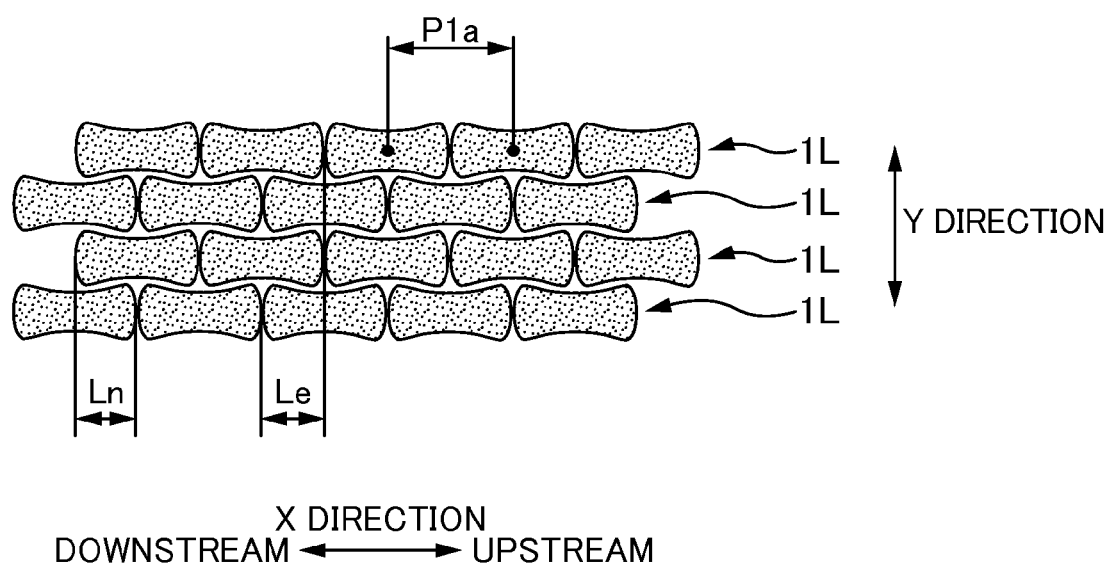
FIG. 6 is a schematic plan view in a case of four napkin lines 1L, as an example of an even number of lines.

Therefore, if such a positional relationship has already been established, it is not necessary to enlarge the arrangement pitch P1a. For example, the number of the napkin lines 1L is even such as four lines shown in FIG. 6, the foregoing positional relationship has already been established without enlarging the arrangement pitch P1a. So, the enlarging is not performed. On the other hand, if the number of napkin line 1L is odd such as five lines, the enlarging is needed. Thus, in the example of FIG. 5, the arrangement pitch P1a is enlarged. Then, the napkins 1, 1 . . . are transported downstream in the X direction towards the second process with remaining in a state where the arrangement pitch P1a is enlarged.

In the second process, a napkin group 1G is formed by specifying one napkin 1 of each napkin line 1L based on a predetermined correlation pattern and correlating the specified napkins 1. Based on this correlation pattern, from the napkin line 1L on one end in the Y direction to the napkin line 1L on the other end, an adjacent napkin 1 positioned obliquely upstream in the X direction is sequentially specified. Thus, from the napkin line 1L on one end in the Y direction to the napkin line 1L on the other end, the adjacent napkin 1 positioned obliquely upstream in the X direction is sequentially correlated as a napkin 1 belonging to the same napkin group 1G. Thereby, formed is a napkin group 1G which includes five napkins 1. Then, napkin groups 1G, 1G . . . are sorted alternatively into two transportation routes along the X direction. As shown in FIG. 5, five napkins 1, 1 . . . constituting a napkin group 1G are transported downstream in the X direction along the transportation route assigned to the napkins. At this stage, the napkins 1, 1 . . . are arranged in a line at an anglle to the X direction, in which the position of a napkin 1 in the Y direction is sequentially shifted as the napkin 1 is located more upstream in the X direction.

Incidentally, the arrangement of napkins 1 before enlarging the foregoing arrangement pitch P1a is different from the arrangement after enlarging, by the amount of the enlarging. Strictly speaking, the shape of the correlation pattern before the enlarging is slightly different from that of the correlation pattern after enlarging. However, according to the definition of the foregoing correlation pattern, specified are the same napkins 1 for forming a napkin group 1G, whether the enlarging has been performed or not. Thus, it can be said that the formation of the napkin group 1G based on the correlation pattern defined as mentioned above is performed for the arrangement of napkins 1 before enlarging, that is, the zig zag arrangement mentioned above, which is a state before the first process (the state shown in the right upper end of FIG. 5). Unless otherwise specifically noted, in the following description, the term "correlation pattern" means the correlation pattern after the arrangement pitch P1a is enlarged.

In the third process, all napkins 1 of the napkin groups 1G and 1G that are being transported in the foregoing transportation route are simultaneously rotated by 90° about their respective substantial planar centers C1 (their substantial centers C1 of the plane determined by the X direction and the Y direction). Thereby, as shown in FIG. 5, the longitudinal direction of all napkins 1 belonging to each napkin group 1G changes simultaneously from the X direction to the Y direction. While remaining as they are, the napkin groups 1G and 1G are transported downstream in the X direction towards the fourth process. Thereby, napkins 1, 1 . . . of each napkin group 1G are transported towards the fourth process in a state where their longitudinal direction are in the Y direction and their positions in the Y direction are different (that is, the napkins are arranged in a oblique line).

In the fourth process, the positions in the Y direction of the napkins 1, 1 . . . belonging to the same napkin group 1G are aligned, while maintaining the relative positional relationship in the X direction between the napkins 1, 1 . . . . Thereby, the napkins 1, 1 . . . of the napkin group 1G are arranged in a line along the X direction.

In this example, the napkin 1 located at the center in the Y direction (this is also located at the center in the X direction) is located at the same position in the Y direction as the transport path of the subsequent individual-wrapping process. Therefore, in this process, the napkin 1 located at the center in the Y direction is the napkin 1 located in the stable refererence position. The napkins 1, 1 . . . located on both sides in the Y direction with respect to the refererence position are sliding towards the center, which is the refererence position in the Y direction. Thereby, all napkins 1, 1 . . . belonging to the same napkin group 1G are aligned in the Y direction. The napkins 1, 1 . . . of the napkin group 1G are transported downstream in the X direction with being arranged in a line in the X direction.

At this stage, the longitudinal direction of the napkins 1 has already been in the Y direction. That is, when the foregoing sliding has been completed, the napkin group 1G has become transported in lateral-direction flowing. Therefore, changing the transporting configuration from longitudinal-direction flowing to lateral-direction flowing has been completed.

Figure 7:
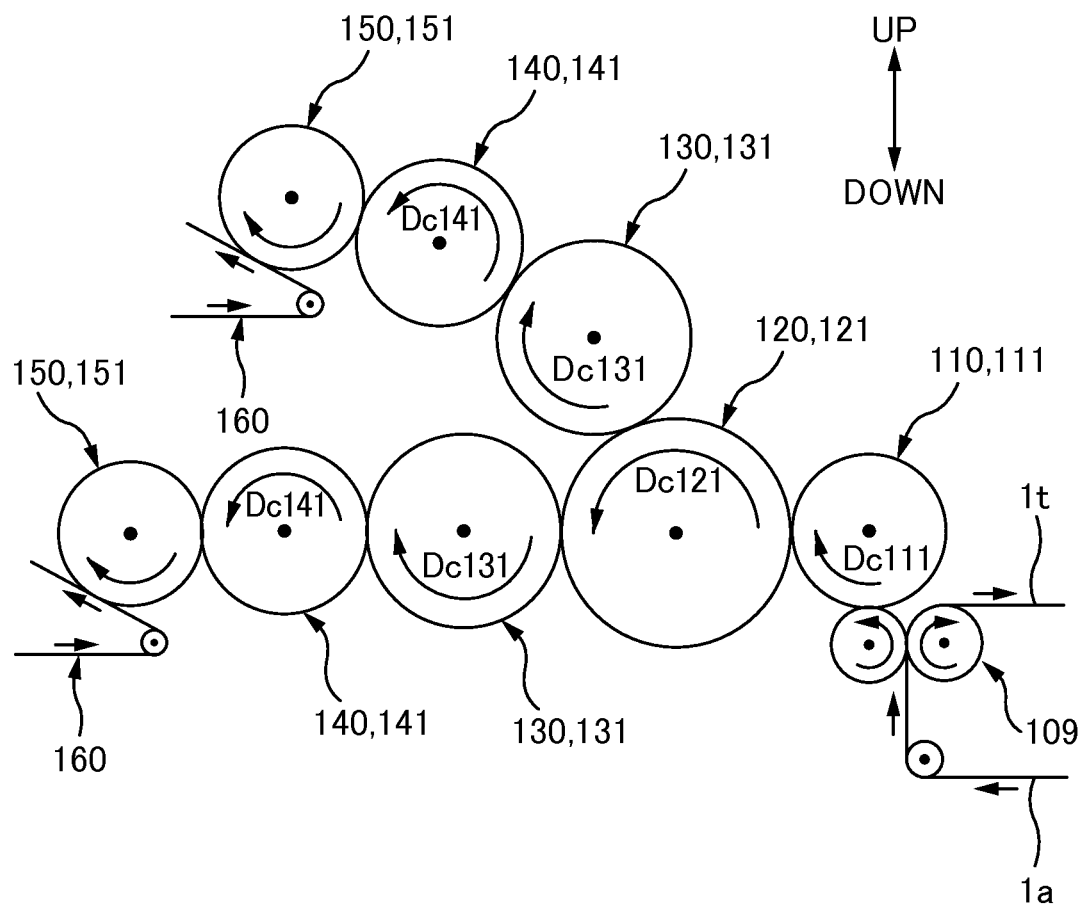
FIG. 7 is a schematic side view of a configuration which realizes the transporting-configuration change process according to the second embodiment.

The foregoing transporting-configuration change process, as shown the schematic side view in FIG. 7, is realized by arranging continuously a plurality of rotating drum devices 110, 120, 130, and 140 in the X direction, for example. The rotating drum devices 110, 120, 130, and 140 each have their own rotating drums 111, 121, 131, and 141 that each have substantially a cylindrical shape and that are driven and rotated about their own rotational axes along the Y direction (a direction perpendicular to the paper surface in FIG. 7). The rotating drums 111, 121, 131, and 141 each have a plurality of sucking sections 112, 122, 132, and 142 each of which can suck and hold a single napkin 1 on its outer circumferential surface. While holding sucked napkins 1, the sucking sections 112, 122, 132, and 142 move together respectively with the rotating drums 111, 121, 131, and 141 in the circumferential directions Dc111, Dc121, Dc131, and Dc141 of the rotating drums 111, 121, 131, and 141 according to the rotation of the rotating drums 111, 121, 131, and 141. Thereby, the napkins 1 are transported in the circumferential directions Dc111, Dc121, Dc131, and Dc141 of the rotating drums 111, 121, 131, and 141.

The rotating drum devices 110, 120, 130, and 140 receive napkins 1 from a device such as the adjacent rotating drum device on the upstream at their own receiving positions which are set at predetermined positions in the circumferential directions Dc111, Dc121, Dc131, and Dc141. After transporting the napkins 1 along the circumferential directions Dc111, Dc121, Dc131, and Dc141, the rotating drum devices 110, 120, 130, and 140 deliver the napkins 1 to the adjacent rotating drum device on the downstream at their own delivery positions which are set at predetermined positions in the circumferential directions Dc111, Dc121, Dc131, and Dc141. The receiving, transporting, and delivering by all rotating drum devices 110, 120, 130, and 140 realize transportation of napkins 1 in the X direction in the foregoing first to fourth processes. That is, the circumferential directions Dc111, Dc121, Dc131, and Dc141 of the rotating drum devices 110, 120, 130, and 140 correspond to the X direction for the foregoing transportation.

It should be noted that, in order to smoothly receive and deliver a napkin 1 between the rotating drum devices 110, 120, 130, and 140, the peripheral speeds of the rotating drums 111, 121, 131, and 141 are set to substantially the same value. That these peripheral speeds are set to the same value are realized by adjusting the rotation radii of the rotating drums 111, 121, 131, and 141, or adjusting the number of sucking sections 112, 122, 132, and 142 on their own outer circumferential surfaces.

Further, the rotating drum devices 110, 120, 130, and 140 each have a function specific thereto so as to be basically responsible for any one of the foregoing first to fourth processes, or so as to cooperate with the adjacent rotating drum device for being responsible for any one of the foregoing first to fourth processes. Thus, each of the rotating drum devices 110, 120, 130, and 140 performs the one of the first to fourth processes which the device itself is responsible for basically during the period of time after reception of each napkin 1 and before delivery to the rotating drum device adjacent on the downstream. Or, it is performed at the time of delivery.

For example, the operation for the first process (enlarging the arrangement pitch P1a) is performed by the rotating drum device 110 (hereinafter referred to as a pitch-changing drum device 110), which is located most upstream in the X direction. The operation for the second process (forming of napkin groups 1G) is performed by both of the rotating drum device 120 (hereinafter referred to as a first transfer drum device 120) and the rotating drum device 130 (hereinafter referred to as a 90° turning drum device 130); the rotating drum device 120 is located downstream from and adjacent to the pitch-changing drum device 110, and the rotating drum device 130 is located downstream from and adjacent to the first transfer drum device 120. The operation for the third process (an operation in which the longitudinal direction of napkins 1 is oriented to the Y direction) is performed by the 90° turning drum device 130, and the operation for the fourth process (aligning the positions of napkins 1 in the Y direction) is performed by the rotating drum device 140 (hereinafter referred to as a slide drum device 140), which is located downstream from and adjacent to the 90° turning drum device 130.

In this example, the rotating drum 151 of a second transfer drum device 150 is further disposed downstream from and adjacent to the slide drum device 140. Through the rotating drum 151, the napkins 1 on the slide drum device 140 transfer onto a belt conveyor 160 that transports the napkins 1 to the individual-wrapping process. However, the second transfer drum device 150 is not an essential component. The napkins 1 may be directly delivered from the slide drum device 140 to the belt conveyor 160.

The rotating drum devices 110, 120, 130, and 140 will be described below.

Figure 8A:
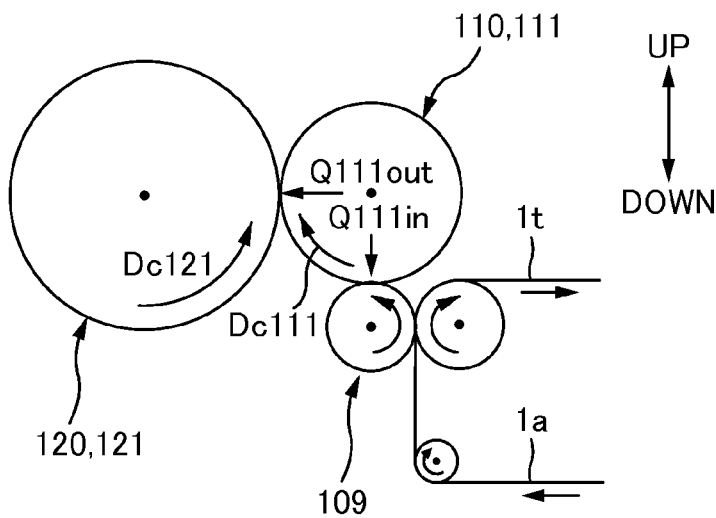
FIG. 8A is a schematic side view of a pitch-changing drum device 110.
Figure 8B:
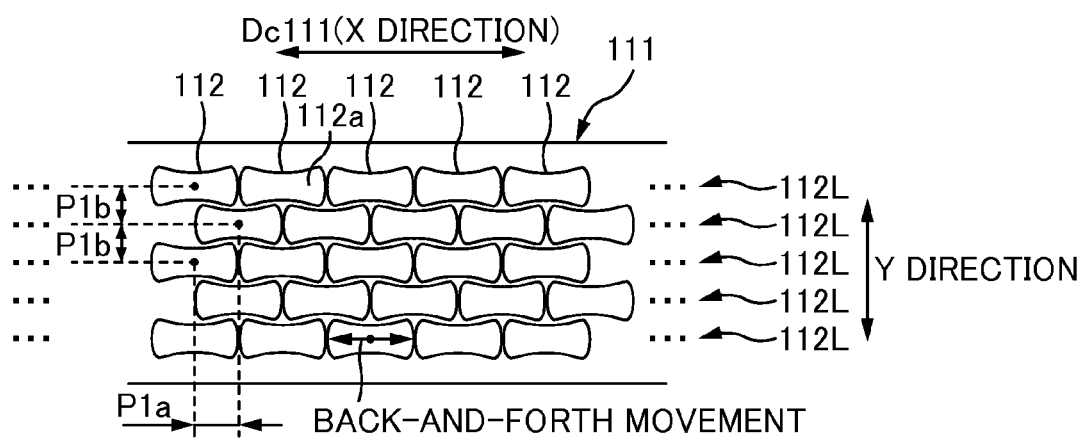
FIG. 8B is a schematic elevation of the outer circumferential surface of a rotating drum 111 before enlarging the arrangement pitch P1a of holding pads 112.

As mentioned above, the first process in which the arrangement pitch P1a is enlarged is performed by a pitch-changing drum device 110. FIG. 8A is a schematic side view thereof. On the outer circumferential surface of the rotating drum 111 of the pitch-changing drum device 110, holding pads 112 (not shown in FIG. 8A) serving as the sucking sections 112 are disposed for each napkin 1 so as to be able to suck the napkin 1. That is, as shown in FIG. 8B, which is a schematic elevation of the outer circumferential surface of the rotating drum 111, the following configuration is provided in order to receive from the die-cutter roll device 109 napkins 1, 1 . . . which are arranged in zig zag arrangement: on the outer circumferential surface of the rotating drum 111, provided are N holding pad lines 112L (N is an integer of 2 or more; 5 in this example) at a certain pitch P1b in the Y direction, each of holding pad lines 112L including a plurality of the holding pads 112 (8 in this example) arranged in the circumferential direction Dc111.

Figure 8C:
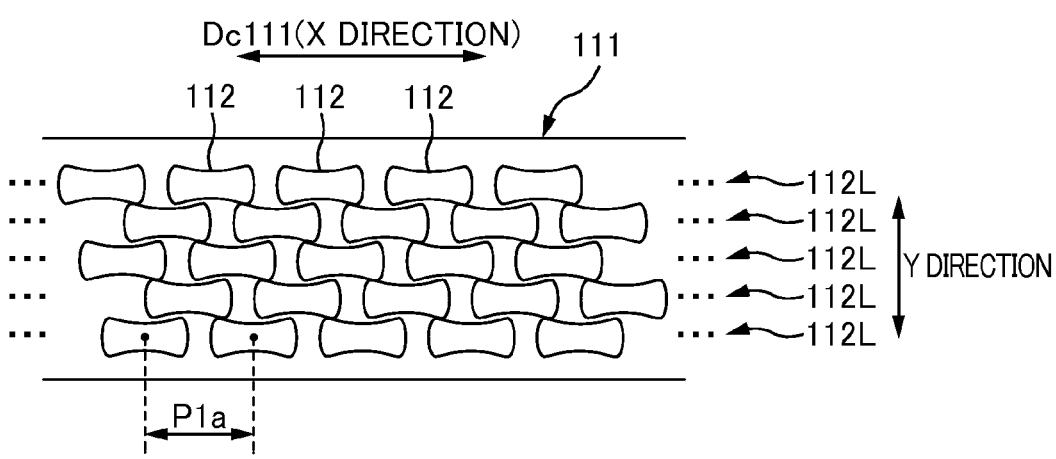

Each holding pad 112 has a holding surface 112a, which has a plurality of suction holes (not shown). By suction through these suction holes, the holding surface 112a sucks and holds a napkin 1 in surface-to-surface contact. Further, holding pads 112 are configured so as to move back and forth with respect to the outer circumferential surface of the rotating drum 111 within the front and back (upstream and downstream) limits in the circumferential direction Dc111. This makes it possible to change an interval between holding pads 112 adjacent in the circumferential direction Dc111 by using a suitable cam mechanism etc. as a power source. By enlarging this interval, the arrangement pitch P1a is enlarged as shown in FIGS. 8B to 8C.

The foregoing enlarging of the arrangement pitch P1a is performed while each holding pad 112 is moving from a receiving position Q111in for the die-cutter roll device 109 in FIG. 8A to a delivery position Q111out for the first transfer drum device 120. Thereby, napkins 1 can be delivered to the first transfer drum device 120 in a state shown in FIG. 8C in which the arrangement pitch P1a is enlarged. On the other hand, while each holding pad 112 is returning from the delivery position Q111out for the first transfer drum device 120 to the receiving position Q111in for the die-cutter roll device 109, an operation is performed in which the enlarged arrangement pitch P1a is shortened and returns to its original size. Thereby, when each holding pad 112 passes the receiving position Q111in for the die-cutter roll device 109, the arrangement pitch P1a is substantially the same as the arrangement pitch P1a of napkins 1 that have been die-cut by the die-cutter roll device 109 and are in zig zag arrangement, as shown in FIG. 8B. As a result, holding pads 112, 112 . . . can receive smoothly napkins 1, 1 . . . from the die-cutter roll device 109.

Figure 9A:
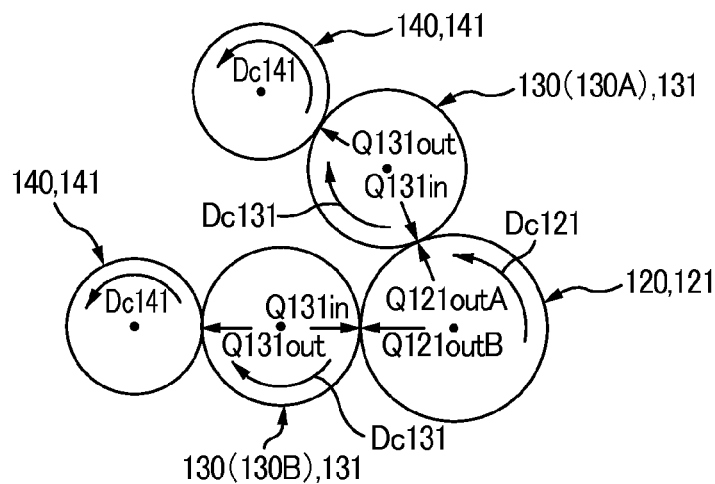
FIG. 9A is a schematic side view of a first transfer drum device 120 and 90° turning drum devices 130 and 130.
Figure 9B:
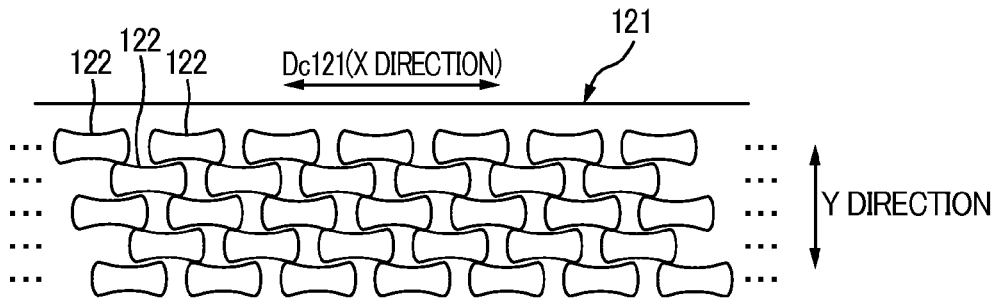
FIG. 9B is a schematic elevation of the outer circumferential surface of the rotating drum 121 of the first transfer drum device 120.

The forming of napkin groups 1G, which is the second process, is performed by the first transfer drum device 120 and 90° turning drum device 130 which are located downstream from and adjacent to the pitch-changing drum device 110. FIG. 9A is a schematic side view thereof. The first transfer drum device 120 has a plurality of sucking sections 122, 122 . . . (not shown in FIG. 9A) which suck napkins 1 on the outer circumferential surface of the rotating drum 121 thereof. FIG. 9B is a schematic elevation of the outer circumferential surface of the rotating drum 121. The sucking sections 122 are provided on the outer circumferential surface of the rotating drum 121 in the same arrangement as the arrangement of the napkins 1 after enlarging the arrangement pitch P1a. This makes it possible to receive smoothly from the pitch-changing drum device 110 napkins 1 whose arrangement pitch P1a has been enlarged. Note that the sucking sections 122 serve as suction areas in which a plurality of suction holes (not shown) are formed on the outer circumferential surface of the rotating drum 121, and the sucking sections 122 suck and hold napkins 1 by suction through the suction holes.

On the other hand, two 90° turning drum devices 130 are provided and face to the outer circumferential surface of the rotating drum 121 of the first transfer drum device 120; these 90° turning drum devices 130 are respectively disposed at a position Q121outA and Q121outB in the circumferential direction Dc121 of the outer circumferential surface. Thereby, the napkin groups 1G, 1G . . . on the outer circumferential surface of the first transfer drum device 120 can be alternatively sorted into two paths. Hereinafter, the 90° turning drum device 130 located upstream of the first transfer drum device 120 in the circumferential direction Dc121 is also referred to as a first turning drum device 130A, and the 90° turning drum device 130 located downstream is also referred to as a second turning drum device 130B.

Figure 9C:
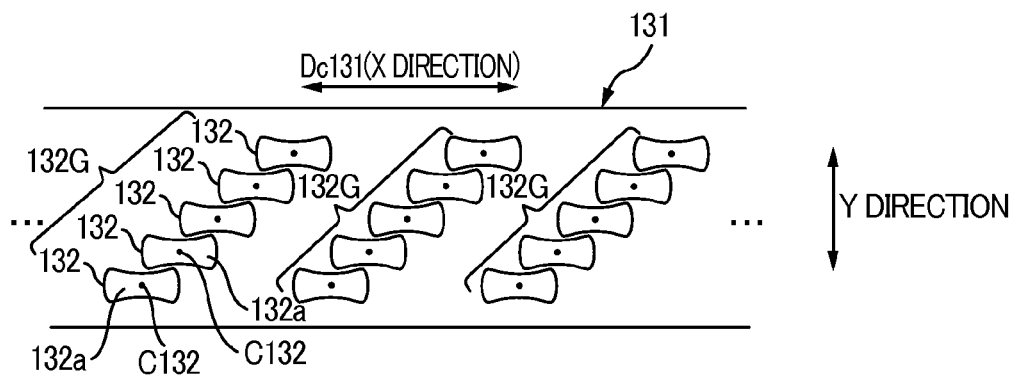
FIG. 9C is a schematic elevation of the outer circumferential surface of the rotating drum 131 of the 90° turning drum device 130, in which holding pads 132, 132 . . . spin by 90° so that the longitudinal direction thereof becomes in the X direction.

The first turning drum device 130A and second turning drum device 130B have substantially the same configuration. That is, the main bodies of both devices are the rotating drums 131 and 131. As shown in FIG. 9C, which is a schematic elevation of the outer circumferential surface of the rotating drum 131, both devices include as sucking sections 132(not shown in FIG. 9A) a plurality of holding pads 132, 132 . . . on their own outer circumferential surface, the holding pads suck and hold napkins 1, The holding pads 132, 132 . . . of the first turning drum device 130A are arranged at a same pitch in a circumferential direction Dc131 on the outer circumferential surface of the rotating drum 131. A set of N holding pads 132, 132 . . . (five pads in this example) arranged in the oblique correlation pattern mentioned above forms a holding pad group 132G. A plurality of the holding pad groups 132G (five groups in this example) are arranged in the circumferential direction Dc131 of the outer circumferential surface of the rotating drum 131. This makes it possible to receive the napkins 1, 1 . . . according to the correlation pattern from the outer circumferential surface of the first transfer drum device 120, and to form the napkin groups 1G on the outer circumferential surface of the first turning drum device 130A.

Similarly, the holding pads 132, 132, . . . of the second turning drum device 130B are arranged at a same pitch in the circumferential direction Dc131 on the outer circumferential surface of the rotating drum 131, as shown in FIG. 9C, which is a schematic elevation of the outer circumferential surface of the rotating drum 131. A set of N holding pads 132, 132 . . . (five pads in this example) arranged in the oblique correlation pattern mentioned above forms a holding pad group 132G. The same number of the holding pad groups 132G as the groups 132G of the foregoing first turning drum device 130A are arranged in the circumferential direction Dc131 of the outer circumferential surface of the rotating drum 131. Thereby, the holding pads 132, 132, . . . of the second turning drum device 130B receive, according to the correlation pattern, the napkins 1, 1 . . . that remain on the outer circumferential surface of the first transfer drum device 120 after passing a delivery position Q121outA for the first turning drum device 130A. Thus, a napkin group 1G can be formed on the outer circumferential surface of the second turning drum device 130B.

On the other hand, each of holding pads 132 of these first and second turning drum devices 130A and 130B are supported by the rotating drum 131 so as to be able to spin around a spin axis C132 along a radial direction of the rotating drum 131, as shown in FIG. 9C. Further, the spin axis C132 is coaxially fixed substantially to the planar center of the holding surface 132a of the holding pad 132 that is to hold a napkin 1 in surface-to-surface contact. The normal direction of the holding surface 132a is in the radial direction.

Figure 9D:
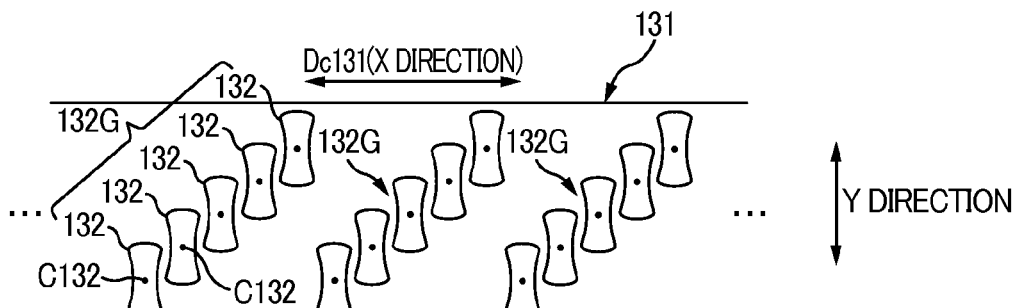
FIG. 9D is a schematic elevation of the outer circumferential surface of the rotating drum 131 in which the holding pads 132, 132 . . . spin by 90° so that the longitudinal direction thereof becomes in the Y direction.

Therefore, as shown in FIG. 9D, spinning of the holding pads 132 by an amount of 90° with a power source such as a suitable cam mechanism makes it possible to change the longitudinal direction of napkins 1 to the Y direction from the X direction, which is the circumferential direction Dc131 of the rotating drum 131. Thus, it is possible to perform the operation in which the longitudinal direction of napkins 1 is oriented to the Y direction, which is the operation for the third process.

As shown in FIG. 9A, the foregoing orientation operation is performed while each holding pad 132 is moving from a receiving position Q131in for the first transfer drum device 120 to a delivery position Q131out for the slide drum device 140. Thereby, napkins 1 can be delivered to the slide drum device 140 with the orientation of the napkins 1 in which the longitudinal direction thereof is in the Y direction. On the other hand, while each holding pad 132 is returning from the delivery position Q131out for the slide drum device 140 to the receiving position Q131in for the first transfer drum device 120, the holding pad 132 spins by 90° so that the longitudinal direction of the holding pad 132 changes from the Y direction to the X direction. Thereby, the holding pads 132 can receive napkins 1 smoothly from the first transfer drum device 120 in a state where the longitudinal direction of the holding pads 132 is in the longitudinal direction of the napkins 1 which are delivered from the first transfer drum device 120.

The foregoing "the operation in which the longitudinal direction of napkins 1 is oriented to the Y direction" is performed for each of the first and second turning drum devices 130A and 130B. The operations for these devices are different in the following points: the delivery positions Q121outA and Q121outB on the circumferential direction Dc121 of the first transfer drum device 120 are different at which napkins 1 are delivered to the 90° turning drum devices 130A and 130B; and the 90° turning drum devices 130A and 130B deliver napkins 1 respectively to the slide drum devices 140 and 140. For aspects other than those described above, the first and second turning drum devices 130A and 130B are the same.

The aligning of the positions of napkins 1 in the Y direction, which is the fourth process, is performed by the foregoing slide drum devices 140 and 140 that are respectively disposed for the first turning drum device 130A and the second turning drum device 130B, as shown in FIG. 7.

Both of the slide drum devices 140 and 140 have the same configuration. Therefore, it goes without saying that the following description for the slide drum device 140 located downstream from and adjacent to the first turning drum device 130A is applied to the slide drum device 140 located downstream from and adjacent to the second turning drum device 130B.

Figure 10A:
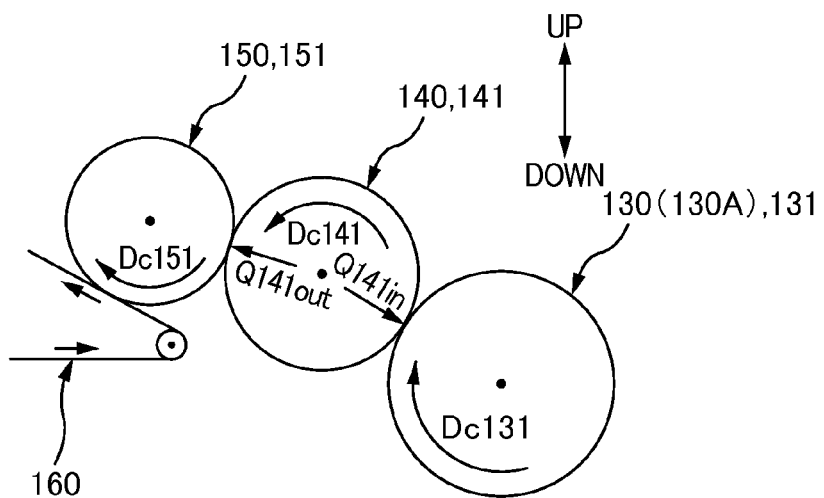
FIG. 10A is a schematic side view of a slide drum device 140.
Figure 10B:
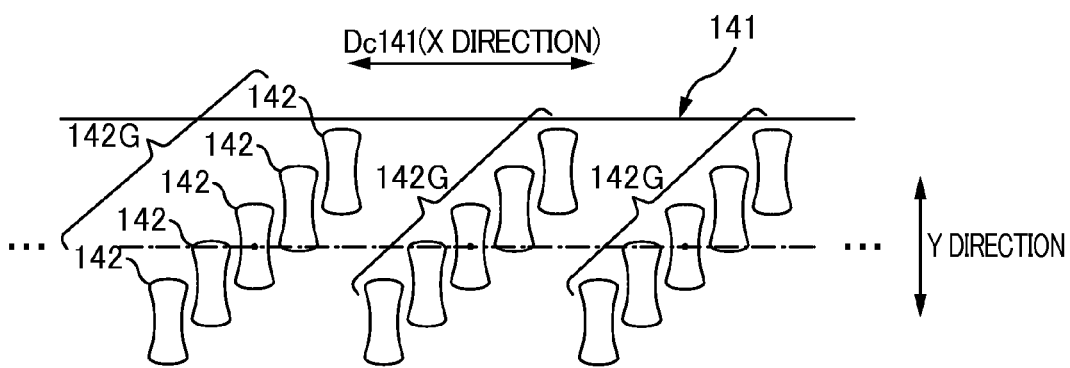
FIG. 10B is a schematic elevation of the outer circumferential surface of the rotating drum 121 before aligning the positions of holding pads 142, 142 . . . in the Y direction.

FIG. 10A is a schematic side view of the slide drum device 140. On the outer circumferential surface of the rotating drum 141 of the slide drum device 140, holding pads 142 that each suck and hold a napkin 1 are provided as sucking sections 142 (not shown in FIG. 10A). FIG. 10B is a schematic elevation of the outer circumferential surface of the rotating drum 121. The holding pads 142 are arranged at a same pitch in a circumferential direction Dc141 on the outer circumferential surface of the rotating drum 141; the longitudinal direction of the holding pads 142 is in the Y direction. A set of N holding pads 142, 142 . . . (five pads in this example) which are adjacent in the circumferential direction Dc141 forms a holding pad group 142G. A plurality of the holding pad group 142G (four sets in this example) are arranged in the circumferential direction Dc141 of the outer circumferential surface of the rotating drum 141.

The holding pad groups 142G respectively correspond to the napkin groups 1G. That is, the central holding pad 142 of a holding pad group 142G in the circumferential direction Dc141 is responsible for the stable napkin 1; and the holding pads 142, 142, 142, and 142 located on both sides in the circumferential direction Dc141 are responsible for the napkins 1, 1, 1 and 1 that should slide in the Y direction. Thus, the central holding pad 142 is immovably fixed to the outer circumferential surface of the rotating drum 141; and the holding pads 142, 142, 142, and 142 located on both sides in the circumferential direction Dc141 are configured so as to move back and forth in the Y direction, where a suitable cam mechanism etc. is used as a power source.

With the holding pad groups 142G having the foregoing configuration, it is possible to align the positions of the napkins 1 of a napkin group 1G in the Y direction as follows.

Figure 10C:
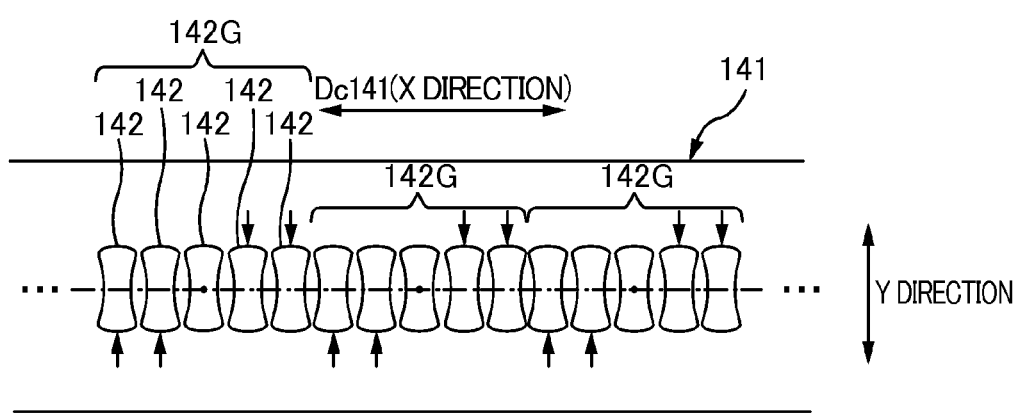
FIG. 10C is a schematic elevation of the outer circumferential surface of the rotating drum 121 after aligning the positions of the holding pads 142, 142 . . . in the Y direction.

Suppose that a holding pad group 142G passes a receiving position Q141in for the first turning drum device 130A shown in FIG. 10A, that is, the napkin group 1G is received from the first turning drum device 130A. At this stage, as a result of the sliding, the holding pads 142 belonging to the holding pad group 142G are located at the positions defined by the foregoing oblique correlation pattern, as shown in FIG. 10B. Therefore, the holding pads 142 can sequentially receive napkins 1 smoothly from the first turning drum device 130A. Thereafter, until the holding pads 142 holding the napkins 1 reach a delivery position Q141out for the second transfer drum device 150, the holding pads 142, 142 . . . except for stable holding pad 142 sequentially slide towards the center in the Y direction. Thereby, as shown in FIG. 10C, the holding pads 142, 142 . . . of the holding pad group 142G are aligned in the Y direction. As a result, when passing the delivery position Q141out, the napkins 1, 1 . . . of the napkin group 1G held by this holding pad group 142G are arranged in a line in the X direction and the napkin group 1G is delivered to the second transfer drum device 150. Thereafter, the napkin group 1G is transported in lateral-direction flowing.

Incidentally, after passing the delivery position Q141out, the holding pads 142 sequentially slide towards the ends in the Y direction (outwardly) until the holding pads 142 reach the receiving position Q141in for the first turning drum device 130A. Thereby, the holding pads 142, 142 . . . of the holding pad group 142G return to a state where the holding pads are arranged in the foregoing oblique correlation pattern, as shown in FIG. 10B.

Other Embodiments

While the embodiments according to the invention are described above, the invention is not limited to the embodiments and can be altered as described below.

In the foregoing embodiment, a finished product of the napkin 1 is provided as an example of a workpiece 1 of an absorbent article. However, the workpiece 1 is not required to be a finished product. That is, the workpiece 1 may be a semifinished product, which is a semi-finished product of an absorbent article.

In the foregoing embodiment, a napkin 1 having three-layer structure is described. However, this invention is not limited thereto. A napkin 1 of multi-layer structure having four or more layers may be employed.

Reference Signs List 1 napkin (workpiece), 1G napkin group (workpiece group), 1L napkin line (workpiece line), 1R napkin line in lateral-direction flowing,
1a continuous sheet,
1c longitudinal central section, 1e longitudinal end section, 1f end section in lateral direction,
1t die-cut chip,
3 surface sheet, 4 liquid-absorbing sheet, 5 back face sheet, 7 wrapping sheet,
9 die-cutter roll device, 9c belt conveyor,
10 widening conveyor, 12 conveyor belt,
20 attach conveyor, 22 conveyor belt, 24 claw,
32 the X-direction conveying mechanism, 33 transporting cord, 33P transporting cord pair,
35 dropping mechanism, 35a pusher bar , 35b power source,
38 the Y-direction conveying mechanism, 39 conveyor belt,
109 die-cutter roll device,
110 pitch-changing drum device, 111 rotating drum,
112 holding pad (sucking section), 112a holding surface, 112L holding pad line,
120 first transfer drum device, 121 rotating drum, 122 sucking section,
130 90° turning drum device,
130A first turning drum device, 130B second turning drum device,
131 rotating drum,
132 holding pad (sucking section), 132a holding surface, 132G holding pad group,
140 slide drum device, 141 rotating drum,
142 holding pad (sucking section), 142G holding pad group,
150 second transfer drum device, 151 rotating drum,
160 belt conveyor,
S35 dropping position,
Q111in receiving position, Q111out delivery position,
Q121outA delivery position, Q121outB delivery position,
Q131in receiving position, Q131out delivery position,
Q141in receiving position, Q141out delivery position,
S1d downstream-end position, S1u upstream-end position, C132 spin axis, C1 planar center

The invention claimed is:

1. A method for changing a transporting configuration of a workpiece of an absorbent article, in which the transporting configuration is changed from longitudinal-direction flowing to lateral-direction flowing, wherein longitudinal-direction flowing is a flowing direction parallel to a longitudinal axis of the workpiece, and lateral-direction flowing is a flowing direction parallel to a lateral axis of the workpiece,
the workpiece having a shape in which a longitudinal central section is narrower in the lateral direction of the workpiece than longitudinal end sections of the workpiece,
the method comprising:
transporting a plurality of workpieces in longitudinal-direction flowing,
the plurality of workpieces being transported in a state where
the longitudinal end sections of each workpiece are adjacent to the central section of another workpiece that is adjacent in the lateral direction of the respective workpieces, and
the plurality of workpieces form N workpiece lines (N is an integer of 2 or more) arranged in the lateral direction, each of the workpiece lines including a plurality of the workpieces along the longitudinal direction, wherein the longitudinal direction is parallel to the respective longitudinal axes of the respective workpieces;
forming each workpiece group including N workpieces by correlating, based on a predetermined correlation pattern, the N workpieces respectively belonging to different workpiece lines of the N workpiece lines that are transported in the longitudinal-direction flowing,
the forming of the workpiece group being performed by correlating, based on the correlation pattern, workpieces that are arranged side by side in the lateral direction of the respective workpieces; and
changing a transporting configuration of the workpieces of the workpiece group from the longitudinal-direction flowing to the lateral-direction flowing, the changing being performed for the each workpiece group, wherein
in the changing of the transporting configuration for each workpiece group from the longitudinal-direction flowing to the lateral-direction flowing:
group directions of the workpieces belonging to respective workpiece groups that are being transported in the longitudinal-direction flowing is changed from a direction parallel to the longitudinal direction of the workpieces of the group to a direction perpendicular to the longitudinal direction of the workpieces of the group, and
the workpieces are aligned so that the workpieces are in a same position in the longitudinal direction.

2. A method for changing a transporting configuration of a workpiece of an absorbent article according to claim 1, wherein
in the forming of the workpiece group based on the correlation pattern,
from a workpiece line on one end to a workpiece line on the other end in a lateral direction of the workpieces that are being transported in the longitudinal-direction flowing, workpieces which are sequentially adjacent to obliquely upstream are correlated as workpieces belonging to a same workpiece group.

* * * * *